United States Patent
Himmler et al.

(10) Patent No.: US 8,507,688 B2
(45) Date of Patent: Aug. 13, 2013

(54) PROCESS FOR PREPARING ARYL- AND HETEROARYLACETIC ACID DERIVATIVES

(75) Inventors: Thomas Himmler, Odenthal (DE); Lukas J. Gooβen, Kaiserslautern (DE); Bettina Zimmermann, Clausen (DE)

(73) Assignee: Bayer CropScience AG (DE)

( * ) Notice: Subject to any disclaimer, the term of this patent is extended or adjusted under 35 U.S.C. 154(b) by 98 days.

(21) Appl. No.: 13/009,453

(22) Filed: Jan. 19, 2011

(65) Prior Publication Data

US 2011/0184180 A1 Jul. 28, 2011

Related U.S. Application Data

(60) Provisional application No. 61/296,081, filed on Jan. 19, 2010.

(30) Foreign Application Priority Data

Jan. 19, 2010 (EP) .................................... 10151081

(51) Int. Cl.
C07D 213/00 (2006.01)

(52) U.S. Cl.
USPC .......................................................... 546/339

(58) Field of Classification Search
None
See application file for complete search history.

(56) References Cited

U.S. PATENT DOCUMENTS 5,994,274 A 11/1999 Fischer et al.
2005/0176987 A1 8/2005 Goossen

OTHER PUBLICATIONS

Goossen, L., Chem. Comm. 2001 p. 669-70.*
Paetzold, E. et al., J. Mol. Catal. 2000 vol. 152, p. 69-76.*
Agnelli, F. and Sulikowski, G.A., "Synthesis of Arylacetates by the Palladium-Catalyzed Cross-Coupling of Aryl Bromides and Copper(II) Enolates," *Tetrahedron Lett.* 39:8807-8810, Elsevier Science Ltd., England (1998).
Bellfna, F. and Rossi, R., "Transition Metal-Catalyzed Direct Arylation of Substrates with Activated sp³-Hybridized C—H Bonds and Some of Their Synthetic Equivalents with Aryl Halides and Pseudohalides," *Chem. Rev.* 110:1082-1146, American Chemical Society, United States (2010).
Carfagna, C., et al., "Palladium-Catalyzed Coupling Reactions of Aryl Triflates or Halides with Ketene Trimethylsilyl Acetals. A New Route to Alkyl 2-Arylalkanoates," *J. Org. Chem*, 56:261-263, American Chemical Society, United States (1991).
Chaussard, J., et al., "Use of Sacrificial Anodes in Electrochemical Functionalization of Organic Halides," *Synthesis* 1990:369-381, Georg Thieme Verlag KG, United States (1990).
Durandetti, M., et al., "Nickel-Catalyzed Direct Electrochemical Cross-Coupling between Aryl Halides and Activated Alkyl Halides," *J. Org. Chem.* 61:1748-1755, American Chemical Society, United States (1996).

Fauvarque, J.F. and Jutand, A., "Catalsis of the Arylation of the Reformatsky Reagent by Palladium or Nickel Complexes. Synthesis of Aryl Acid Esters," *J. Organomet. Chem.* 177:273-281, Elsevier Sequoia S.A, Switzerland (1979).
Genet, J.P. and Savignac, M., "Recent developments of palladium(0) catalyzed reactions in aqueous medium," *J. Organomet. Chem.* 576:305-317, Elsevier Science S.A., Switzerland (1999).
Giordano, C., et al., "Synthesis of Anti-Inflammatory α-Arylalkanoic Acids by 1,2-Aryl Shift," *Angew. Chem. Int Ed Engl.* 23:413-419, Verlag Chemie GmbH, Germany (1984).
Gooβen, L.J., "Pd-catalyzed synthesis of arylacetic acid derivatives from boronic acids," *Chem Commun*:669-670, The Royal Society of Chemistry, England (2001).
Johansson, C.C.C, and Colacot, T.J., "Metallkatalysierte α-Arylierungen von Carbonylen und verwandten Molekülen: aktuelle Trends bei der C-C-Kupplung über C-H-Funktionalisierung," *Angew. Chem.* 122:686-718, Wiley-VCH Verlag GmbH & Co. KGaA, Weinheim, Germany (2010).
Kawatsura, M. and Hartwig, J.F., "Simple, Highly Active Palladium Catalysts for Ketone and Malonate Arylation: Dissecting the Importance of Chelation and Steric Hindrance," *J. Am. Chem. Soc.*, 121:1473-1478, American Chemical Society, United States (1999).
Kosugi, M. et al., "Palladium-catalyzed Displacement of Aryl Halide by Tin Analogue of Reformatsky Reagent," *Bull. Chem. Soc. Jpn.* 58:3383-3384, The Chemical Society of Japan, Japan (1985).
Leake, W.W. and Levine, R., "The Phenylation of Esters by Reaction with Bromobenzene and Sodium Amide," *J. Amer. Chem. Soc.* 81:1627-1630, American Chemical Society, United States (1959).
Lu T-Y., et al., "Palladium-catalyzed cross-coupling reaction of aryldioxaborolane with 2-bromo-N,N-dimethylacetamide," *Tetrahedron Lett.* 44:1587-1590, Elsevier Science Ltd., England (2003).
Millard, A.A. and Rathke, M.W., "A Nickel Catalyst for the Arylation and Vinylation of Lithium Ester Enolates," *J. Amer. Chem. Soc.*, 99:4833-4835, American Chemical Society, United States (1977).
Naidan, V.M. and Dombrovskii, A.V., "A New Method for the Production of Arylacetic Acids," *Zhurnal Obshchei Khimii* 34:1474-1477, Chernovits State University, Ukraine (1964).
Okuro, K., et al., "Copper-Catalyzed Reaction of Aryl Iodides with Active Methylene Compounds," *J. Org. Chem.* 58:7606-7607, American Chemical Society, United States (1993).
Orsini, F. and Pelizzoni, F., "Pd (0)-Mediated Cross-Coupling of Reformatsky Reagents With Vinyl- and Aryl Triflates," *Synthetic Communications* 17:1389-1402, Marcel Dekker, Inc., United States (1987).
Özdemir, I., et al., "Synthesis of arylacetic acid derivatives from diethyl malonate using in situ formed palladium(1,3-dialkylimidazolidin-2-ylidene) catalysts," *Tetrahedron Lett.* 45:5823-5825, Elsevier Ltd, England (2004).

(Continued)

*Primary Examiner* — Janet Andres
*Assistant Examiner* — Heidi Reese
(74) *Attorney, Agent, or Firm* — Sterne, Kessler, Goldstein & Fox P.L.L.C.

(57) ABSTRACT

The present invention relates to a process for preparing α-arylmethylcarbonyl compound of the formula (III), characterized in that aryl- and heteroarylacetic acids and derivatives thereof of the formula (I) are reacted with α-halomethylcarbonyl compounds of the formula (II) in the presence of a palladium catalyst, of a phosphine ligand, of an inorganic base and of a phase transfer catalyst, optionally using an organic solvent.

9 Claims, No Drawings

(56) References Cited

OTHER PUBLICATIONS

Paetzold, E. and Oehme, G., "Efficient two-phase Suzuki reaction catalyzed by palladium complexes with water-soluble phosphine ligands and detergents as phase transfer reagents," *J. Mol. Catal. A: Chem.* 152: 69-76, Elsevier Science B.V, Netherlands (2000).

Sakamoto, T., et al., "Synthesis of Methyl 2-(Heteroaryl)Propanoates Via Palladium-Catalyzed Reaction," *Heterocycles* 36:2509-2512, Elsevier Science B.V., Netherlands (1993).

Semmelhack, M.F., et al., "Total Synthesis of the *Cephalotaxus* Alkaloids. A Problem in Nucleophilic Aromatic Substitution," *J. Amer. Chem. Soc.* 97:2507-2516, American Chemical Society, United States (1975).

Van Leeuwen, M. and McKillop, A., "A Study of the Ferrous Ion-initiated $S_{RN}1$ Reactions of Halogenoarenes with *tert*-Butyl Acetate and *N*-Acylmorpholine Enolates," *J. Chem, Soc. Perkin* 1:2433-2440, Chemical Society, London, England (1993).

Zaugg, H.E., et al., "Naphthoquinone Antimalarials. XIV. 2-Hydroxy-3-aryl-1,4-naphthoquinones," *J. Amer. Chem. Soc,* 70:3224-3228, American Chemical Society, United States (1948).

International Search Report for International Patent Application No. PCT/EP2011/050456, European Patent Office, Rijswijk, Netherlands, mailed on Mar. 9, 2011.

Johansson, C.C.C. and Thomas, J. C., "Metal-Catalyzed α-Arylation of Carbonyl and Related Molecules: Novel Trends in C—C Bond Formation by C—H Bond Functionalization," *Angew. Chem. Int. Ed.* 49:676-707, Wiley-VCH Verlag GmbH & Co. KGaA, Germany (2010) (English language version).

\* cited by examiner

PROCESS FOR PREPARING ARYL- AND HETEROARYLACETIC ACID DERIVATIVES

The invention relates to a process for preparing aryl- and heteroarylacetic acids and derivatives thereof by reacting aryl- or heteroarylboronic acid derivatives with α-haloacetic acids or derivatives thereof in the presence of a palladium catalyst, of a base and of a phase transfer catalyst. This process enables the preparation of a multitude of functionalized aryl- and heteroarylacetic acids and derivatives thereof. It can additionally also be employed for preparation of other α-arylcarbonyl compounds.

Typically, phenylacetic acid derivatives are prepared in multistage syntheses which usually have a low group tolerance. The preparation can be effected, for example, proceeding from acetophenones by a Willgerodt-Kindler reaction (see, for example, H. E. Zaugg et al., *J. Amer. Chem. Soc.* 70 (1948) 3224-8). This method, however, gives rise to large amounts of sulphur-containing wastes. In addition, highly malodorous volatile sulphur compounds may occur.

A further method for preparing arylacetic acids proceeds from benzyl bromides or chlorides. Sodium cyanide, for example, is used to prepare the corresponding nitriles therefrom, and they are subsequently hydrolysed. The benzyl bromides or chlorides required can be obtained, for example, by bromo- or chloromethylation of the corresponding aromatics. However, a disadvantage here is that the occurrence of highly carcinogenic compounds such as bis(chloromethyl)ether or bis(bromomethyl)ether cannot be ruled out, and so a high level of safety measures have to be taken in industry. Moreover, the halomethylation of substituted aromatics leads in many cases to isomer mixtures.

The carbonylation of benzyl halides in the presence of alcohols likewise affords phenylacetic esters. The already mentioned limited availability of benzyl halides and the necessity to use toxic CO gas, in some cases even under elevated pressure, are further disadvantages of this process.

Another procedure which has already become known is to ketalize α-chloroacetophenones and then to subject the ketals to a rearrangement reaction (C. Giordano et al., *Angew. Chem.* 96 (1984) 413-9). The α-chloroacetophenones are obtained either by chlorinating acetophenones or directly by a Friedel-Crafts acylation of the aromatic in question with chloroacetyl chloride. This again gives rise to the disadvantage that the Friedel-Crafts acylations on substituted aromatics frequently proceed unselectively.

A further known method for preparing phenylacetic acids consists in diazotizing a corresponding aniline in the first step, reacting the resulting diazonium compound with vinylidene chloride in the second step, and then reacting the trichloroethyl or bromodichloroethyl compound thus obtained in the third step with water or alcohols to give the arylacetic acid or esters thereof (see, for example, V. M. Naidan and A. V. Dombrovskii, *Zhurnal Obshchei Khimii* 34 (1984)1469-73; EP-A-835243). However, this reaction generally affords good yields only with those anilines which bear electron-withdrawing radicals on the aromatic ring and in which the amino group is not sterically blocked.

Also known is the reaction of bromobenzenes with chloroacetic acid derivatives in the presence of stoichiometric amounts of silver or copper at 180-200° C. A disadvantage of these processes is the high temperature, which rules out use in the case of thermally sensitive compounds, the low yield and the use of stoichiometric amounts of expensive metals which are difficult to reprocess.

The reaction of aryl Grignard compounds with α-haloacetic acid derivatives likewise leads to phenylacetic acid derivatives. However, a disadvantage is the extremely limited tolerance for functional groups as a result of the use of highly reactive Grignard compounds, which are difficult to handle.

It has likewise become known to prepare arylacetic acid derivatives by reacting aryl halides with dialkyl malonates with simultaneous dealkoxycarbonylation (*Tetrahedron Lett.* 2004, 45, 5823-5). However, this has the disadvantage that the base required is expensive caesium carbonate.

As an alternative to the processes described, cross-couplings of aryl halides with Reformatsky reagents, tin enolates, copper enolates and other enolates or ketene acetals have also been described (see, for example, *J. Am. Chem. Soc.* 1959, 81, 1627-1630; *J. Organomet. Chem.* 1979, 177, 273-281; *Synth. Comm.* 1987, 17, 1389-1402; *Bull. Chem. Soc. Jpn.* 1985, 58, 3383-3384; *J. Org. Chem.* 1993, 58, 7606-7607; *J. Chem. Soc. Perkin* 1 1993, 2433-2440; *J. Am. Chem. Soc.* 1975, 97, 2507-2517; *J. Am. Chem. Soc.* 1977, 99, 4833-4835; *J. Am. Chem. Soc.* 1999, 121, 1473-78; *J. Org. Chem.* 1991, 56, 261-263, *Heterocycles* 1993, 36, 2509-2512, *Tetrahedron Lett.* 1998, 39, 8807-8810. Reviews of such reactions can be found in: *Chem. Rev.* 2010, 110, 1082-1146 and *Angew. Chem.* 2010, 122, 686-718).

However, the applicability of these processes is limited. For instance, Reformatsky reagents and ketene acetals are difficult to prepare and handle. The use of tin compounds is disadvantageous for toxicological reasons, and the use of stoichiometric amounts of copper causes considerable costs in the disposal. The use of enolates is generally possible only when no further enolizable groups are present in the molecule. For example, ketones are therefore ruled out as substrates for such processes. Some electrochemical processes are likewise known (*Synthesis* 1990, 369-381; *J. Org. Chem.* 1996, 61, 1748-1755), but these processes are disadvantageous owing to the complex reaction regime and the low space-time yields.

Likewise already known is a method for preparing phenylacetic acid derivatives by a palladium-catalysed coupling reaction between widely available, easy-to-handle and stable arylboronic acids and ethyl bromoacetate (L. J. Gooβen, *Chem. Commun.* 2001, 660-70; DE-A-10111262). However, it has not been possible to date to use this process for preparation of sterically demanding, for example 2,6-disubstituted, phenylacetic acid derivatives. *Chem. Commun.* 2001, 660-70 does state that sterically hindered arylboronic acids can also be converted efficiently under the conditions described therein. However, the examples contain only 2-tolylboronic acid as a sterically hindered substrate. More sterically restricted arylboronic acids, for example 2,6-dialkylphenylboronic acids, are not described. In-house tests (see Comparative Example 1) demonstrate that the above-cited method gives only unsatisfactory yields of arylacetic acid derivatives in such cases.

All methods which have become known to date for preparing phenylacetic acid derivatives with sterically demanding substitution accordingly have deficiencies and disadvantages, some of them considerable, which complicate the application thereof. Since phenylacetic acids in general, and among them specifically also those with sterically demanding substitution, are important precursors, for example for active ingredients in crop protection, there is a need for a technically simple and highly efficient method for preparing such compounds.

Surprisingly, a process has now been found for preparing aryl- and heteroarylacetic acids and derivatives thereof from aryl- and heteroarylboronic acid derivatives and α-haloacetic acids and derivatives thereof, which is characterized in that the reaction is performed in the presence of a palladium catalyst, a phosphine, an inorganic base and a phase transfer catalyst.

The discovery that the addition of a phase transfer catalyst has a positive influence on the selectivity of the reaction was not foreseeable and makes the discovery of this process particularly surprising.

By virtue of the use of the phase transfer catalyst, it is possible for the first time to shift the selectivity significantly in favour of the desired product. More particularly, the formation of arenes with protodeborylation is suppressed. Only small proportions of undesired by-products are formed.

Moreover, the addition of the phase transfer catalyst has the effect that the amount of palladium catalyst needed for a very substantial conversion can be lowered significantly. This makes the process much more economically viable than the process known according to the prior art.

The process according to the invention is not restricted to arylboronic acids with sterically demanding substitution. Arylboronic acids with different kinds of substitution can also be converted in better yields under the inventive conditions.

The process according to the invention for preparing aryl- and heteroarylcarbonyl compounds is characterized in that aryl- or heteroarylboronic acids of the formula (I)

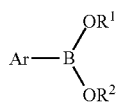

in which
$R^1$ is hydrogen or $C_1$-$C_8$-alkyl,
$R^2$ is hydrogen or $C_1$-$C_8$-alkyl, or
$R^1$ and $R^2$ together with the atoms to which they are bonded are a saturated or unsaturated, substituted or unsubstituted cycle,
Ar is the group

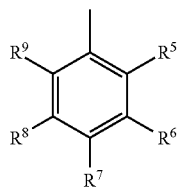

where
$R^5$, $R^6$, $R^7$, $R^8$ and $R^9$ are the same or different and are each independently hydrogen, halogen, optionally halogen-substituted $C_1$-$C_6$-alkyl, $C_1$-$C_6$-alkoxy, phenyl, —CO—$C_1$-$C_3$-alkyl, —COO—$C_1$-$C_6$-alkyl or —COO—$C_6$-$C_{10}$-aryl,
the Ar radical may additionally also be a heteroaromatic radical such as 2-pyridyl, 3-pyridyl, 4-pyridyl, 2-furyl, 3-furyl, 2-thienyl or 3-thienyl, or
the Ar radical may also be 1- or 2-naphthyl,
are reacted with α-halomethylcarbonyl compounds of the formula (II)

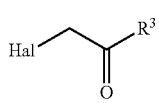

in which
Hal is halogen,
$R^3$ is hydroxyl, in each case optionally substituted $C_1$-$C_8$-alkyl, $C_1$-$C_8$-alkoxy, phenyl, aryl, phenoxy or aryloxy, or $NR^4R^{4'}$,
where $R^4$ and $R^{4'}$ are the same or different and are each independently hydrogen, $C_1$-$C_4$-alkyl, or phenyl optionally substituted by $C_1$-$C_3$-alkyl which may be substituted by fluorine or chlorine, or by nitro, cyano or di-$C_1$-$C_3$-alkylamino, or, together with the nitrogen atom to which they are bonded, are a saturated or unsaturated, substituted or unsubstituted cycle,
in the presence of a palladium catalyst, of a phosphine ligand, of an inorganic base, and of a phase transfer catalyst, optionally using an organic solvent,
to give α-arylmethylcarbonyl compounds of the formula (III)

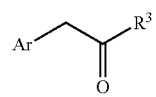

in which Ar and $R^3$ are each as defined above.

This reaction is illustrated by the following reaction equation:

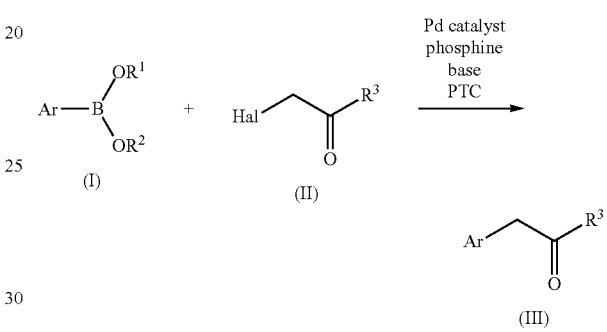

PTC = phase transfer catalyst

Preferred substituents and ranges for the radicals shown in the formulae mentioned above and below are elucidated hereinafter:
$R^1$ is preferably hydrogen or $C_1$-$C_4$-alkyl,
$R^2$ is preferably hydrogen or $C_1$-$C_4$-alkyl, or
$R^1$ and $R^2$, together with the atoms to which they are bonded, are preferably optionally $C_1$-$C_4$-alkyl- or aryl-(especially phenyl-)substituted $C_2$-$C_3$-alkanediyl,
$R^3$ is preferably hydroxyl, optionally fluorine-substituted $C_1$-$C_4$-alkyl, $C_1$-$C_4$-alkoxy, in each case optionally substituted phenyl, phenoxy, or $NR^4R^{4'}$,
where $R^4$ and $R^{4'}$ are preferably the same or different and are each independently hydrogen, methyl, ethyl, i-propyl, n-propyl, or optionally methyl-, ethyl-, i-propyl-, n-propyl-, $CF_3$—, $C_2F_5$—, $C_3F_7$—, nitro-, cyano-, N(methyl)$_2$-, N(ethyl)$_2$-, N(n-propyl)$_2$-, N(i-propyl)$_2$-substituted phenyl, or, together with the nitrogen atom to which they are bonded, are a saturated or unsaturated, substituted or unsubstituted, 5- or 6-membered cycle,
Ar is preferably 1- or 2-naphthyl or the group

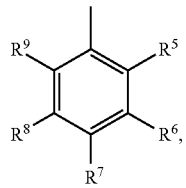

where
$R^5$, $R^6$, $R^7$, $R^8$ and $R^9$ are preferably the same or different and are each independently hydrogen, fluorine, chlorine, optionally fluorine-substituted $C_1$-$C_4$-alkyl, $C_1$-$C_4$-alkoxy, phenyl, —CO—$C_1$-$C_3$-alkyl, —COO—$C_1$-$C_4$-alkyl or —COO—$C_6$-$C_8$-aryl, Hal is preferably fluorine, chlorine, bromine or iodine.

$R^1$ is more preferably hydrogen, methyl, ethyl, i-propyl or n-propyl, $R^2$ is more preferably hydrogen, methyl, ethyl, i-propyl or n-propyl, or $R^1$ and $R^2$ together with the atoms to which they are bonded are more preferably optionally mono- to tetra-methyl-substituted $C_2$-alkanediyl, optionally mono- to hexa-methyl-substituted $C_3$-alkanediyl (emphasis is given to —$CH_2C(CH_3)_2CH_2$—, —$C(CH_3)_2C(CH_3)_2$—), $R^3$ is more preferably methyl, ethyl, i-propyl, n-propyl, $CF_3$, $C_2F_5$, $C_3F_7$, methoxy, ethoxy, i-propoxy, n-propoxy or tert-butoxy, in each case optionally substituted phenyl, or $NR^4R^{4'}$, where $R^4$ and $R^{4'}$ are more preferably the same or different and are each independently hydrogen, methyl, ethyl, i-propyl, n-propyl or, together with the nitrogen atom to which they are bonded, are a saturated, unsubstituted, 5- or 6-membered cycle, Ar is more preferably 1-naphthyl or the group

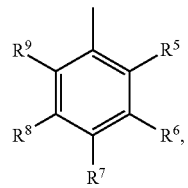

where $R^5$, $R^6$, $R^7$, $R^8$ and $R^9$ are more preferably the same or different and are each independently hydrogen, fluorine, chlorine, methyl, ethyl, i-propyl, n-propyl, $CF_3$, $C_2F_5$, $C_3F_7$, methoxy, ethoxy, phenyl, —CO-methyl, —CO-ethyl, —COO-methyl, —COO-ethyl or —COO-phenyl, Hal is more preferably chlorine, bromine or iodine.

$R^1$ is most preferably hydrogen, $R^2$ is most preferably hydrogen, $R^3$ is most preferably methoxy, ethoxy, tert-butoxy, phenyl or $NR^4R^{4'}$, where $R^4$ and $R^{4'}$, together with the nitrogen atom to which they are bonded, are a saturated, unsubstituted 6-membered cycle, Ar is most preferably 1-naphthyl, phenyl, 2,6-dimethylphenyl, 2,4,6-trimethylphenyl, 4-acetylphenyl, 4-chloro-2,6-dimethylphenyl, 2,6-diethyl-4-methylphenyl, 4-methoxyphenyl, 4-ethoxycarbonylphenyl, Hal is most preferably bromine.

The general radical definitions and elucidations given above or those given within areas of preference may be combined with one another, i.e. including combinations between the particular ranges and preferred ranges. They apply correspondingly to the end products and to the intermediates.

The boronic acids of the formula (I) are known in principle or can be prepared by known methods, for example from the corresponding bromoaromatics, magnesium metal and trimethyl borate.

The boronic acids can optionally also be obtained in situ by reacting corresponding aryl halides or heteroaryl halides either with a diboron compound or a borane in the presence of a palladium catalyst according to the prior art.

The compounds of the formula (II) are known in principle or can be prepared by known methods.

The bases used in the process according to the invention are inorganic bases such as alkali metal or alkaline earth metal hydroxides, carbonates, bicarbonates, oxides, phosphates, hydrogenphosphates, fluorides or hydrogenfluorides. Preference is given to using alkali metal and alkaline earth metal phosphates, carbonates or fluorides, and particular preference to using potassium fluoride, potassium carbonate and potassium phosphate. Emphasis is given to potassium fluoride.

In the process according to the invention, 1 to 10 equivalents of the particular base are used. Preferably, 2-7 equivalents of the base are used.

The palladium catalysts used in the process according to the invention are palladium(II) salts, for instance palladium chloride, bromide, iodide, acetate, acetylacetonate, which may optionally be stabilized by further ligands, for example alkyl nitriles, or Pd(0) species such as palladium on activated carbon, $Pd(PPh_3)_4$, bis(dibenzylideneacetone)palladium or tris(dibenzylideneacetone)dipalladium. Preference is given to bis(dibenzylideneacetone)palladium, tris(dibenzylideneacetone)dipalladium, palladium chloride, palladium bromide and palladium acetate; emphasis is given to bis(dibenzylideneacetone)palladium.

The amount of palladium catalyst used in the process according to the invention is 0.001 to 5 mole percent, based on arylboronic acid used. Preferably, 0.005 to 3 mole percent is used; particular preference is given to 0.01 to 1 mole percent.

The phosphine ligands used in the process according to the invention are ligands $PR^{10}R^{11}R^{12}$ where the $R^{10}$, $R^{11}$ and $R^{12}$ radicals are each hydrogen, linear and branched $C_1$-$C_8$-alkyl, vinyl, aryl, or heteroaryl from the group of pyridine, pyrimidine, pyrrole, thiophene or furan, which may in turn be substituted by further substituents from the group of linear and branched $C_1$-$C_8$-alkyl or $C_6$-$C_{10}$-aryl, linear and branched $C_1$-$C_8$-alkyloxy or $C_1$-$C_{10}$-aryloxy, halogenated linear and branched $C_1$-$C_8$-alkyl or halogenated $C_6$-$C_{10}$-aryl, linear and branched $C_1$-$C_8$-alkyl or $C_6$-$C_{10}$-aryloxycarbonyl, linear and branched $C_1$-$C_8$-alkylamino, linear and branched $C_1$-$C_8$-dialkylamino, $C_1$-$C_8$-arylamino, $C_1$-$C_8$-diarylamino, formyl, hydroxyl, carboxyl, cyano and halogens such as F, Cl, Br and I.

Preferred phosphine ligands are triphenylphosphine, tri(1-naphthyl)phosphine and tri(o-tolyl)-phosphine. Emphasis is given to tri(1-naphthyl)phosphine and tri(o-tolyl)phosphine.

Alternatively, it is also possible to use defined palladium complexes which have been obtained beforehand from the abovementioned ligands in one or more process steps.

In the process according to the invention, 1-20 molar equivalents of phosphine are used, based on the amount of palladium used. Preference is given to using 1-4 molar equivalents.

In the process according to the invention, a phase transfer catalyst from the group of the quaternary ammonium salts, the quaternary phosphonium salts and the metal salts which have in turn been solubilized by crown ethers or cryptands is used.

This phase transfer catalyst preferably has the general formula (IV)

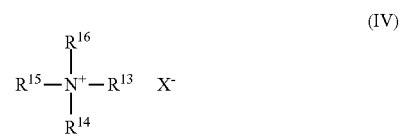

The $R^{13}$, $R^{14}$, $R^{15}$ and $R^{16}$ radicals are the same or different and are each independently $C_1$-$C_{28}$-alkyl, optionally branched $C_1$-$C_{28}$-alkyl, $C_6$-$C_{10}$-aryl or benzyl.

The X radical is halogen, hydrogensulphate, sulphate, dihydrogenphosphate, hydrogenphosphate, phosphate or acetate.

X is preferably bromine, chlorine, fluorine, hydrogensulphate, sulphate, phosphate and acetate.

Examples of such phase transfer catalysts include tetrabutylammonium fluoride, chloride, bromide, iodide, acetate, tetraethylammonium iodide, benzyltriethylammonium bromide, dodecyltrimethylammonium bromide and methyltridecylammonium chloride (Aliquat 336). Emphasis is given to tetrabutylammonium fluoride, acetate, and benzyltriethylammonium bromide.

The amount of phase transfer catalyst in the process according to the invention is between 1 and 50 mole percent, based on arylboronic acid. Preference is given to amounts between 5 and 20 mole percent.

The process according to the invention is performed at temperatures of −20° C. to 200° C., preferably at 0° C. to 150° C. and more preferably at 20° C. to 120° C.

The process according to the invention can be performed in the presence of a solvent or in substance. Preference is given to working in the presence of a solvent. Preferred solvents are saturated aliphatic hydrocarbons, alicyclic hydrocarbons, aromatic hydrocarbons, alcohols, amides, sulphoxides, sulphonates, nitriles, esters or ethers.

For example, the solvents used may be pentane, hexane, heptane, octane, cyclohexane, toluene, xylenes, ethylbenzene, mesitylene, dioxane, tetrahydrofuran, dibutyl ether, methyl t-butyl ether, diisopropyl ether, diethylene glycol dimethyl ether, methanol, ethanol, propanol, isopropanol, methyl acetate, ethyl acetate, t-butyl acetate, dimethylformamide, diethylformamide, N-methylpyrrolidone, dimethylacetamide, dimethyl sulphoxide, sulpholane, acetonitrile, propionitrile or water.

Particular preference is given to using aromatic hydrocarbons, amides, esters and ethers. Very particular preference is given to using ethers.

The process according to the invention is typically performed at standard pressure, but can also be performed at reduced or elevated pressure.

To isolate the aryl- and heteroarylacetic acids and derivatives thereof prepared in accordance with the invention, the reaction mixture, after the reaction has ended, is worked up, preferably by distillation and/or by extraction. Preference is given to working up the reaction mixture by extraction and subsequent distillation.

The process according to the invention is illustrated by the examples which follow, without being restricted thereto.

EXAMPLE 1

Ethyl 2,6-dimethylphenylacetate

A 25 ml three-neck flask with magnetic stirrer, reflux condenser and dropping funnel is initially charged with 20 ml of tetrahydrofuran (THF) which has been dried over molecular sieve. The THF is heated to 50° C. while passing argon through for a few minutes, and then cooled again to room temperature. Still under argon, the following are now added: 17.2 mg [0.03 mmol=0.3 mol %] of bis(dibenzylideneacetone)palladium, 27.4 mg of P(o-tolyl)$_3$ (tri-o-tolylphosphine) [0.09 mmol], 2.91 g of potassium fluoride (dried over P$_2$O$_5$ at 140° C.), 272 mg [1 mmol=10 mol %] of benzyltriethylammonium bromide, 1.5 g [10 mmol] of 2,6-dimethylphenylboronic acid and 2.56 g [15 mmol] of ethyl bromoacetate. This mixture is stirred under reflux in a gentle argon stream for 24 hours. Then it is filtered through a little Celite, and the filtercake is washed three times with 20 ml each time of ethyl acetate. The combined filtrates are extracted by shaking with 20 ml of 1 N hydrochloric acid. The aqueous phase is re-extracted twice with 20 ml of ethyl acetate each time. The combined organic phases are then washed with 20 ml of saturated aqueous NaCl solution, dried and concentrated. This gives 2.16 g of an oil which, according to GC-MS, as well as 8.9 area % of m-xylene, contains 72.9 area % of ethyl 2,6-dimethylphenylacetate. This corresponds to a yield of 81.9% of theory.

COMPARATIVE EXAMPLE 1

Ethyl 2,6-dimethylphenylacetate

A 25 ml three-neck flask with magnetic stirrer, reflux condenser and dropping funnel is initially charged with 20 ml of tetrahydrofuran (THF) which has been dried over molecular sieve, and 0.36 ml of water. The mixture is heated to 50° C. while passing argon through for a few minutes, and then cooled again to room temperature. Still under argon, the following are now added: 17.2 mg [0.03 mmol=0.3 mol %] of bis(dibenzylideneacetone)palladium, 27.4 mg of P(o-tolyl)$_3$ [0.09 mmol], 2.91 g of potassium fluoride (dried over P$_2$O$_5$ at 140° C.), 1.5 g [10 mmol] of 2,6-dimethylphenylboronic acid and 2.56 g [15 mmol] of ethyl bromoacetate. This mixture is stirred under reflux in a gentle argon stream for 24 hours. Then it is filtered through a little Celite, and the filtercake is washed three times with 20 ml each time of ethyl acetate. The combined filtrates are extracted by shaking with 20 ml of 1 N hydrochloric acid. The aqueous phase is re-extracted twice with 20 ml of ethyl acetate each time. The combined organic phases are then washed with 20 ml of saturated aqueous NaCl solution, dried and concentrated. This gives 1.59 g of an oil which, according to GC-MS, as well as 10.7 area % of m-xylene, contains 56.6 area % of ethyl 2,6-dimethylphenylacetate. This corresponds to a yield of 46.8% of theory.

EXAMPLES 2 TO 10

General Experimental Description

The boronic acid (1.00 mmol), Pd(dba)$_2$(bis(dibenzylideneacetone)palladium) (1.73 mg, 3.00 μmol), tri-o-tolylphosphine (2.74 mg, 9.00 μmol), benzyltriethylammonium bromide (27.8 mg, 0.10 mmol) and potassium fluoride (174 mg, 3.00 mmol) are introduced into a 20 ml vial under atmospheric oxygen. The vessel is closed, and three times evacuated and refilled with nitrogen. Ethyl bromoacetate (167 mg, 166 μl, 1.50 mmol) and 2 ml of THF (dry, degassed with argon) are added while stirring. The reaction mixture is stirred at 60° C. for 24 hours. After the reaction time has expired, the mixture is cooled, 50 μl of n-tetradecane are added, a 0.25 ml sample is taken and washed in 3 ml of ethyl acetate and 2 ml of water, and 0.25 ml is withdrawn, filtered through a pipette containing Celite/basic alumina, and then analysed by GC.

Workup: The reaction solution is filtered through a Celite/basic alumina (1:2) combination. The filtercake is washed with ethyl acetate. The filtrate is concentrated and purified by means of column chromatography (5:1, hexane/ethyl acetate, silica gel). This leaves the product.

EXAMPLE 2

Ethyl 2,4,6-trimethylphenylacetate

Ethyl 2,4,6-trimethylphenylacetate was prepared according to the general experimental method from 2,4,6-trimethylphenylboronic acid (164 mg, 1.00 mmol). After workup by column chromatography (hexane/ethyl acetate, 5:1), ethyl 2,4,6-trimethylphenylacetate is obtained as a colourless liquid in a yield of 62% of theory. $^1$H NMR (200 MHz, CDCl$_3$): δ=6.89 (s, 2H), 4.10-4.25 (m, 2H), 3.67 (s, 2H), 2.27-2.37 (m, 9H), 1.27 (t, J=7.1 Hz, 3H) ppm; $^{13}$C NMR (50 MHz, CDCl$_3$): δ=171.9, 137.4, 136.8, 129.3, 129.2, 61.1, 35.6, 21.3, 20.6, 14.7 ppm; MS (70 eV), m/z (%): 206 (23) [M$^+$], 160, (7), 133 (100), 105 (10) 91 (11); IR (NaCl): ν=2978 (m), 2867 (w), 1732 (s), 1157 (m), 1031 (m) cm$^{-1}$.

EXAMPLE 3

Ethyl 4-acetylphenylacetate

Ethyl 4-acetylphenylacetate was prepared by the general experimental method from 4-acetylphenylboronic acid (164 mg, 1.00 mmol). After workup by column chromatography (hexane/ethyl acetate, 5:1), ethyl 4-acetylphenylacetate is obtained as a colourless solid in a yield of 60% of theory. $^1$H NMR (400 MHz, CDCl$_3$): δ=7.90 (d, J=8.2 Hz, 2H), 7.37 (d, J=8.5 Hz, 2H), 4.11-4.17 (m, 2H), 3.66 (s, 2H), 2.58 (s, 3H), 1.20-1.27 (m, 3H) ppm; $^{13}$C NMR (151 MHz, CDCl$_3$): δ=197.7, 170.8, 139.5, 136.0, 129.6, 128.6, 61.1, 41.3, 26.6, 14.2 ppm; MS (70 eV), m/z (%): 192 (100), 164 (16), 134 (14), 105 (19), 89 (11); IR (KBr): ν=2981 (w), 1735 (s), 1682 (m), 1274 (m), 1178 (m) cm$^{-1}$; elemental analysis: (theor): C=69.89, H=6.84, (exp): C=69.95, H=6.99. Melting point: 55-56° C.

EXAMPLE 4

Ethyl 4-chloro-2,6-dimethylphenylacetate

Ethyl 4-chloro-2,6-dimethylphenylacetate was prepared by the general experimental method from 4-chloro-2,6-dimethylphenylboronic acid (186 mg, 1.00 mmol). This involved using 290 mg [5 mmol] of KF and 418 mg [2.5 mmol] of ethyl bromoacetate. After workup by column chromatography (hexane/ethyl acetate, 5:1), ethyl 4-chloro-2,6-dimethylphenylacetate is obtained as a colourless liquid in a yield of 68% of theory. $^1$H NMR (400 MHz, CDCl$_3$): δ=7.02 (s, 2H), 4.13 (q, J=0.7 Hz, 2H), 3.62 (s, 2H), 2.29 (s, 6H), 1.23 (t, J=7.2 HZ, 3H) ppm; $^{13}$C NMR (101 MHz, CDCl$_3$): δ=170.8, 139.0, 132.2, 131.6, 130.3, 127.9, 113.6, 60.8, 35.0, 20.1, 14.2 ppm; MS (70 eV), m/z (%): 226 (22) [M$^+$], 180 (9), 153 (100), 115 (17), 91 (11); IR (NaCl): ν=2980 (m), 1733 (s), 1328 (w), 1155 (m), 1030 (m) cm$^{-1}$; elemental analysis: (theor): C=63.58, H=6.67, (exp): C=63.30, H=6.78.

EXAMPLE 5

Ethyl 2,6-diethyl-4-methylphenylacetate

Ethyl 2,6-diethyl-4-methylphenylacetate was prepared by the general experimental method from 2,6-diethyl-4-methylphenylboronic acid (186 mg, 1.00 mmol). This involved using 5.75 mg [0.01 mmol] of Pd(dba)$_2$ and 9.1 mg [0.03 mmol] of P(o-tolyl)$_3$. After workup by column chromatography (hexane/ethyl acetate, 5:1), ethyl 2,6-diethyl-4-methylphenylacetate is obtained as a colourless liquid in a yield of 54% of theory. $^1$H NMR (400 MHz, CDCl$_3$): δ=6.91 (s, 2H), 4.16 (q, J=7.2 Hz, 2H), 3.71 (s, 2H), 2.61-2.69 (m, 4H), 2.32 (s, 3H), 1.19-1.28 (m, 9H) ppm; $^{13}$C NMR (101 MHz, CDCl$_3$): δ=171.9, 143.0, 136.7, 127.2, 127.1, 60.6, 34.0, 26.4, 21.1, 15.1, 14.2 ppm; MS (70 eV), m/z (%): 234 (37) [M$^+$], 161 (100), 147 (33), 133 (40), 119 (13); IR (NaCl): ν=2966 (s), 1739 (s), 1458 (w), 1156 (m), 1032 (m) cm$^{-1}$; elemental analysis: (theor): C=76.88, H=9.46, (exp): C=75.85, H=9.38.

EXAMPLE 6

Ethyl 1-naphthaleneacetate

Ethyl 1-naphthaleneacetate was prepared by the general experimental method from 1-naphthaleneboronic acid (172 mg, 1.00 mmol). After workup by column chromatography (hexane/ethyl acetate, 5:1), ethyl 1-naphthaleneacetate is obtained as a colourless liquid in a yield of 77% of theory. $^1$H NMR (600 MHz, CDCl$_3$): δ=8.04 (d, J=8.3 Hz, 1H), 7.89 (d, J=8.1 Hz, 1H), 7.80-7.84 (m, 1H), 7.55-7.58 (m, 1H), 7.50-7.54 (m, 1H), 7.43-7.47 (m, 2H), 4.16-4.20 (m, 2H), 4.09 (s, 2H), 1.23-1.27 (m, 3H) ppm; $^{13}$C NMR (151 MHz, CDCl$_3$): δ=171.7, 133.9, 132.2, 130.8, 128.8, 128.1, 128.0, 126.4, 125.8, 125.6, 123.9, 61.0, 39.4, 14.3 ppm; MS (70 eV), m/z (%): 214 (100) [M$^+$], 141 (34), 115 (45), 89 (9), 63 (6); IR (NaCl): ν=3047 (w), 2981 (m), 1733 (s), 1173 (m), 1029 (m) cm$^{-1}$, elemental analysis: (theor): C=78.48, H=6.59, (exp): C=78.35, H=6.86.

EXAMPLE 7

Ethyl 4-methoxyphenylacetate

Ethyl 4-methoxyphenylacetate was prepared by the general experimental method from 4-methoxyphenylboronic acid (152 mg, 1.00 mmol). After workup by column chromatography (hexane/ethyl acetate, 5:1), ethyl 4-methoxyphenylacetate is obtained as a colourless liquid in a yield of 77% of theory. $^1$H NMR (200 MHz, CDCl$_3$): δ=7.25 (d, J=8.5 Hz, 2H), 6.91 (d, J=8.7 Hz, 2H), 4.13-4.26 (m, 2H), 3.82 (s, 3H), 3.59 (s, 2H), 1.24-1.26 (m, 3H) ppm; $^{13}$C NMR (50 MHz, CDCl$_3$): δ=172.3, 159.1, 130.7, 126.7, 114.4, 61.1, 55.6, 40.9, 14.6 ppm; MS (70 eV), m/z (%): 194 (24) [M$^+$], 121 (100), 91 (8), 77 (10), 51 (4); IR (NaCl): ν=2981 (m), 2836 (w), 1732 (s), 1513 (s), 1247 (m), 1032 (m) cm$^{-1}$; elemental analysis: (theor): C=68.02, H=7.27, (exp): C=67.91, H=7.18.

EXAMPLE 8

Ethyl 4-ethoxycarbonylphenylacetate 1,4-diethyl 1,4-phenyldiacetate was prepared by the general experimental method from 4-ethoxycarbonylphenylboronic acid (194 mg, 1.00 mmol). After workup by column chromatography (hexane/ethyl acetate, 5:1), 1,4-diethyl 1,4-phenyldiacetate is obtained as a yellow liquid in a yield of 71% of theory. $^1$H NMR (600 MHz, CDCl$_3$): δ=8.12 (d, J=8.6 Hz, 1H), 7.99 (d, J=8.3 Hz, 1H), 7.67 (d, J=8.3 Hz, 1H), 7.34 (d, J=8.1 Hz, 1H), 4.38-4.42 (m, 1H), 4.34-4.37 (m, 1H), 4.12-4.16 (m, 1H), 3.65 (s, 1H), 1.36-1.42 (m, 4H), 1.22-1.26 (m, 2H) ppm; $^{13}$C NMR (151 MHz, CDCl$_3$): δ=170.9, 166.4, 139.2, 130.2, 129.8, 129.4, 129.3, 127.2, 61.1, 61.0, 41.4, 14.4, 14.2 ppm; MS (70 eV), m/z (%): 237 (6) [M$^+$], 191 (39), 163 (100), 135 (39), 118 (13); IR (NaCl): ν=2982 (m), 2938 (w), 1735 (s), 1718 (s) 1277 (s) cm$^{-1}$; elemental analysis: (theor): C=66.09, H=6.83, (exp): C=65.98, H=7.05.

EXAMPLE 9

Ethyl 2,6-dimethylphenylacetate

Ethyl 2,6-dimethylphenylacetate was prepared by the general method using 0.1 mmol of tetrabutylammonium fluoride instead of benzyltriethylammonium bromide in a yield of 63% of theory.

EXAMPLE 10

Ethyl 2,6-dimethylphenylacetate

Ethyl 2,6-dimethylphenylacetate was prepared by the general method using 0.1 mmol of tetrabutylammonium acetate instead of benzyltriethylammonium bromide in a yield of 66% of theory.

EXAMPLE 11

ω-(2,6-Dimethylphenyl)acetophenone 2,6-Dimethylphenylboronic acid (151 mg, 1.01 mmol), ω-bromoacetophenone (299 mg, 1.50 mmol), Pd(dba)$_2$ (5.75 mg, 10.0 μmol), tri-o-tolylphosphine (10.0 mg, 32.9 μmol), benzyltriethylammonium bromide (27.2 mg, 0.10 mmol) and potassium fluoride (323 mg, 5.56 mmol) are introduced into a 20 ml vial under atmospheric oxygen. The vessel is closed, and three times evacuated and refilled with nitrogen. 2 ml of THF (dry, degassed with argon) are added while stirring. The reaction mixture is stirred at 60° C. for 24 hours. After the reaction time has expired, the mixture is cooled, 50 μl of n-tetradecane are added, a 0.25 ml sample is taken and washed in 3 ml of ethyl acetate and 2 ml of water, and 0.25 ml is withdrawn, filtered through a pipette containing Celite/basic alumina and then analysed by GC.

Workup: The reaction solution is filtered through a Celite/basic alumina (1:2) combination. The filtercake is washed with ethyl acetate. The filtrate is concentrated and purified by means of column chromatography (5:1, hexane/ethyl acetate, silica gel). This leaves: ω-(2,6-dimethylphenyl)acetophenone (106 mg, 0.473 mmol, 47% of theory).

$^1$H NMR (400 MHz, CDCl$_3$): δ=8.16 (d, J=7.2 Hz, 2H), 7.66 (d, J=7.4 Hz, 1H), 7.51-7.61 (m, 2H), 7.12-7.21 (m, 3H), 4.45 (s, 2H), 2.30 (s, 6H) ppm; $^{13}$C NMR (101 MHz, CDCl$_3$): δ=196.9, 137.4, 137.0, 133.1, 132.5, 128.7, 128.1, 128.0, 126.9, 39.7 ppm; MS (70 eV), m/z (%): 224 (11) [M$^+$], 119 (9), 106 (8), 105 (100), 91 (9), 77 (33), 51 (11); elemental analysis: (theor): C=85.68, H=7.19, (exp): C=85.39, H=7.22; melting point: 113-114° C.

EXAMPLE 12

N-(Phenylacetyl)piperidine

Benzeneboronic acid (122 mg, 1.00 mmol), Pd(dba)$_2$ (1.73 mg, 3.0 μmol), tri-1-naphthylphosphine (3.71 mg, 9.00 μmol), benzyltriethylammonium bromide (27.2 mg, 0.10 mmol) and potassium fluoride (290 mg, 5.00 mmol) are introduced into a 20 ml vial under atmospheric oxygen. The vessel is closed, and three times evacuated and refilled with nitrogen. N-(Bromoacetyl)piperidine (309 mg, 1.50 mmol) and 2 ml of THF (dry, degassed with argon) are added while stirring. The reaction mixture is stirred at 60° C. for 24 hours. After the reaction time has expired, the mixture is cooled, 50 μl of n-tetradecane are added, a 0.25 ml sample is taken and washed in 3 ml of ethyl acetate and 2 ml of water, and 0.25 ml is withdrawn, filtered through a pipette containing Celite/basic alumina and then analysed by GC.

Workup: The reaction solution is filtered through a Celite/basic alumina (1:2) combination. The filtercake is washed with ethyl acetate. The filtrate is concentrated and purified by means of column chromatography (1:2, hexane/ethyl acetate, silica gel). This leaves N-phenylacetylpiperidine (169 mg, 0.714 mmol, 71% of theory).

$^1$H NMR (600 MHz, CDCl$_3$): δ=7.29 (t, J=7.5 Hz, 2H), 7.19-7.24 (m, 2H), 3.71 (s, 2H), 3.52-3.56 (m, 2H), 3.33-3.37 (m, 2H), 1.60-1.65 (m, 1H), 1.52-1.57 (m, 2H), 1.47-1.52 (m, 2H), 1.30-1.34 (m, 2H) ppm; $^{13}$C NMR (151 MHz, CDCl$_3$): δ=169.3, 135.5, 128.7, 126.6, 48.0, 47.3, 43.3, 42.9, 41.2, 31.0, 26.2, 25.5, 25.4, 24.3 ppm; MS (70 eV), m/z (%): 203 (44) [M$^+$], 112 (100), 91 (41), 84 (14), 69 (57), 65 (18), 41 (29).

The inveniton claimed is:

1. A process for preparing a compound of formula (III)

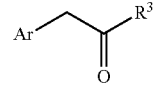

(III)

in which
Ar is the group

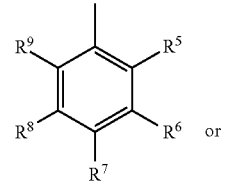

Ar is a heteroaromatic radical or
Ar is 1- or 2-naphthyl,
where $R^5$, $R^6$, $R^7$, $R^8$ and $R^9$ are the same or different and are each independently hydrogen, halogen, optionally halogen-substituted $C_1$-$C_6$-alkyl, $C_1$-$C_6$-alkoxy, phenyl, —CO—$C_1$-$C_3$-alkyl, —COO—$C_1$-$C_6$-alkyl or —COO—$C_6$-$C_{10}$-aryl,
$R^3$ is hydroxyl, in each case optionally substituted $C_1$-$C_8$-alkyl, $C_1$-$C_8$-alkoxy, phenyl, aryl, phenoxy or aryloxy, or NR$^4$R$^{4'}$,
where $R^4$ and $R^{4'}$ are the same or different and are each independently hydrogen, $C_1$-$C_4$-alkyl, phenyl optionally substituted by $C_1$-$C_3$-alkyl which may be substituted by fluorine or chlorine, or by nitro, cyano or di-$C_1$-$C_3$-alkylamino, or, together with the nitrogen atom to which they are bonded, are a saturated or unsaturated, substituted or unsubstituted cycle,
comprising, reacting a compound of formula (I)

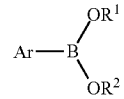

(I)

in which
$R^1$ is hydrogen or $C_1$-$C_8$-alkyl,
$R^2$ is hydrogen or $C_1$-$C_8$-alkyl, or
$R^1$ and $R^2$ together with the atoms to which they are bonded are a saturated or unsaturated, substituted or unsubstituted cycle,
and Ar is as defined above
with a compound of formula (II)

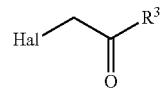

(II)

in which
Hal is halogen,
and $R^3$ is as defined above,
in the presence of a palladium catalyst, a phosphine ligand, an inorganic base, and a phase transfer catalyst, optionally using an organic solvent.

2. The process for preparing the compound of formula (III) according to claim 1, wherein
   $R^1$ is hydrogen or $C_1$-$C_4$-alkyl,
   $R^2$ is hydrogen or $C_1$-$C_4$-alkyl, or
   $R^1$ and $R^2$, together with the atoms to which they are bonded, are optionally $C_1$-$C_4$-alkyl- or aryl-substituted $C_2$-$C_3$-alkanediyl,
   $R^3$ is hydroxyl, optionally fluorine-substituted $C_1$-$C_4$-alkyl, $C_1$-$C_4$-alkoxy, in each case optionally substituted phenyl, phenoxy, or $NR^4R^{4'}$,
   where $R^4$ and $R^{4'}$ are the same or different and are each independently hydrogen, methyl, ethyl, i-propyl, n-propyl, or optionally methyl-, ethyl-, i-propyl-, n-propyl-, $CF_3$-, $C_2F_5$-, $C_3F_7$-, nitro-, cyano-, $N(methyl)_2$-, $N(ethyl)_2$-, $N(n-propyl)_2$-, $N(i-propyl)_2$-substituted phenyl, or, together with the nitrogen atom to which they are bonded, are a saturated or unsaturated, substituted or unsubstituted, 5- or 6-membered cycle,
   Ar is 1- or 2-naphthyl or the group

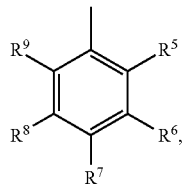

where
   $R^5$, $R^6$, $R^7$, $R^8$ and $R^9$ are the same or different and are each independently hydrogen, fluorine, chlorine, optionally fluorine-substituted $C_1$-$C_4$-alkyl, $C_1$-$C_4$-alkoxy, phenyl, —CO—$C_1$-$C_3$-alkyl, —COO—$C_1$-$C_4$-alkyl or —COO—$C_6$-$C_8$-aryl, and
   Hal is fluorine, chlorine, bromine or iodine.

3. The process for preparing the compound of formula (III) according to claim 1, wherein
   $R^1$ is hydrogen, methyl, ethyl, i-propyl or n-propyl,
   $R^2$ is hydrogen, methyl, ethyl, i-propyl or n-propyl, or
   $R^1$ and $R^2$ together with the atoms to which they are bonded are optionally mono- to tetra-methyl-substituted $C_2$-alkanediyl, optionally mono- to hexa-methyl-substituted $C_3$-alkanediyl,
   $R^3$ is methyl, ethyl, i-propyl, n-propyl, $CF_3$, $C_2F_5$, $C_3F_7$, methoxy, ethoxy, i-propoxy, n-propoxy or tert-butoxy, in each case optionally substituted phenyl, or $NR^4R^{4'}$,
   where $R^4$ and $R^{4'}$ are the same or different and are each independently hydrogen, methyl, ethyl, i-propyl, or n-propyl, or, together with the nitrogen atom to which they are bonded, are a saturated, unsubstituted, 5- or 6-membered cycle,
   Ar is 1-naphthyl or the group

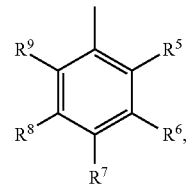

where
   $R^5$, $R^6$, $R^7$, $R^8$ and $R^9$ are the same or different and are each independently hydrogen, fluorine, chlorine, methyl, ethyl, i-propyl, n-propyl, $CF_3$, $C_2F_5$, $C_3F_7$, methoxy, ethoxy, phenyl, —CO-methyl, —CO-ethyl, —COO-methyl, —COO-ethyl or —COO-phenyl, and
   Hal is chlorine, bromine or iodine.

4. The process for preparing the compound of formula (III) according to claim 1, wherein
   $R^1$ is hydrogen,
   $R^2$ is hydrogen,
   $R^3$ is methoxy, ethoxy, tert-butoxy, phenyl or $NR^4R^{4'}$,
   where $R^4$ and $R^{4'}$, together with the nitrogen atom to which they are bonded, are a saturated, unsubstituted 6-membered cycle,
   Ar is 1-naphthyl, phenyl, 2,6-dimethylphenyl, 2,4,6-trimethylphenyl, 4-acetylphenyl, 4-chloro-2,6-dimethylphenyl, 2,6-diethyl-4-methylphenyl, 4-methoxyphenyl, 4-ethoxycarbonylphenyl, and
   Hal is bromine.

5. The process for preparing the compound of formula (III) according to claim 1, wherein the palladium catalyst used is bis(dibenzylideneacetone)palladium, tris(dibenzylidene-acetone)dipalladium, palladium chloride, palladium bromide or palladium acetate.

6. The process for preparing the compound of formula (III) according to claim 1, wherein the phosphine ligand used is triphenylphosphine, tri(1-naphthyl)phosphine or tri(o-tolyl)phosphine.

7. The process for preparing the compound of formula (III) according to claim 1, wherein the base used is potassium fluoride, potassium carbonate or potassium phosphate.

8. The process for preparing the compound of formula (III) according to claim 1, wherein the phase transfer catalyst used is tetrabutylammonium fluoride, chloride, bromide, iodide or acetate, tetraethylammonium iodide, benzyltriethylammonium bromide, dodecyltrimethylammonium bromide or methyltridecylammonium chloride.

9. A process for preparing the compound of formula (III) according to claim 1, wherein Ar is 2-pyridyl, 3-pyridyl, 4-pyridyl, 2-furyl, 3-furyl, 2-thienyl or 3-thienyl.

* * * * *